United States Patent
Bare

(10) Patent No.: US 12,220,518 B2
(45) Date of Patent: *Feb. 11, 2025

(54) TRIPLE SYRINGE AND METHODS OF MAKING PLATELET-ENRICHED PLASMA AND USE THEREOF

(71) Applicant: Arthrex, Inc., Naples, FL (US)

(72) Inventor: Christopher Bare, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/484,844

(22) Filed: Oct. 11, 2023

(65) Prior Publication Data

US 2024/0100236 A1 Mar. 28, 2024

Related U.S. Application Data

(63) Continuation of application No. 17/223,277, filed on Apr. 6, 2021, now Pat. No. 11,806,462, which is a
(Continued)

(51) Int. Cl.
| | |
|---|---|
| *A61M 1/38* | (2006.01) |
| *A61B 5/15* | (2006.01) |
| *A61B 5/153* | (2006.01) |
| *A61K 35/16* | (2015.01) |
| *A61M 1/02* | (2006.01) |

(Continued)

(52) U.S. Cl.
CPC .......... *A61M 1/382* (2013.01); *A61B 5/15003* (2013.01); *A61B 5/150236* (2013.01); *A61B 5/150244* (2013.01); *A61B 5/150251* (2013.01); *A61B 5/150755* (2013.01); *A61B 5/153* (2013.01); *A61K 35/16* (2013.01); *A61M 1/029* (2013.01); *A61M 5/19* (2013.01); *G01N 1/4077* (2013.01); *A61M 2202/0413* (2013.01); *A61M 2202/0415* (2013.01); *A61M 2202/10* (2013.01);
(Continued)

(58) Field of Classification Search
CPC ..................................................... A61M 1/029
See application file for complete search history.

(56) References Cited

U.S. PATENT DOCUMENTS

| | | |
|---|---|---|
| 6,649,072 B2 | 11/2003 | Brandt et al. |
| 8,052,969 B2 | 11/2011 | Buhr et al. |

(Continued)

FOREIGN PATENT DOCUMENTS

WO   WO 2013/140858 A1   9/2013

OTHER PUBLICATIONS

Kunneke et al., Pferdeheilkunde 24, 2008, 4:519-523 (Year: 2008).*
(Continued)

*Primary Examiner* — Qing Xu
(74) *Attorney, Agent, or Firm* — Lathrop GPM LLP; Lisa Hillman

(57) ABSTRACT

A triple syringe system that allows for a larger output of autologous conditioned plasma (ACP) is provided. Autologous blood or bone marrow aspirate can be introduced into a nested set of syringes, which are subjected to centrifugation to obtain two or more of blood or bone marrow fractions including a first fraction and a second fraction. The first fraction can be transferred from the first syringe to the second and third syringes to obtain the ACP.

16 Claims, 5 Drawing Sheets

Related U.S. Application Data continuation of application No. 14/605,657, filed on Jan. 26, 2015, now abandoned.

(60) Provisional application No. 61/931,956, filed on Jan. 27, 2014.

(51) Int. Cl.
*A61M 5/19* (2006.01)
*G01N 1/40* (2006.01)
*C12N 5/078* (2010.01)

(52) U.S. Cl.
CPC .......... *C12N 5/0634* (2013.01); *C12N 5/0641* (2013.01); *Y10T 436/25375* (2015.01)

(56) References Cited

U.S. PATENT DOCUMENTS

| | | |
|---|---|---|
| 9,968,769 B2 | 5/2018 | Sasayama et al. |
| 2006/0273050 A1 | 12/2006 | Higgins et al. |
| 2008/0116421 A1 | 5/2008 | Wang et al. |
| 2015/0073356 A1 | 3/2015 | Sasayama et al. |

OTHER PUBLICATIONS

Stenhouse et al., Skeletal Radiol, 2013, 42:1515-1520 (Year: 2013).*
Deans et al., Journal of Foot & Ankle Surgery, 2012, 51:706-710 (Year: 2012).*
Sampson et al., "Platelet rich injection grafts for musculoskeletal injuries: a review", Current Reviews in Musculoskeletal Medicine, vol. 1, No. 3-4, pp. 165-174, Dec. 1, 2008.

* cited by examiner

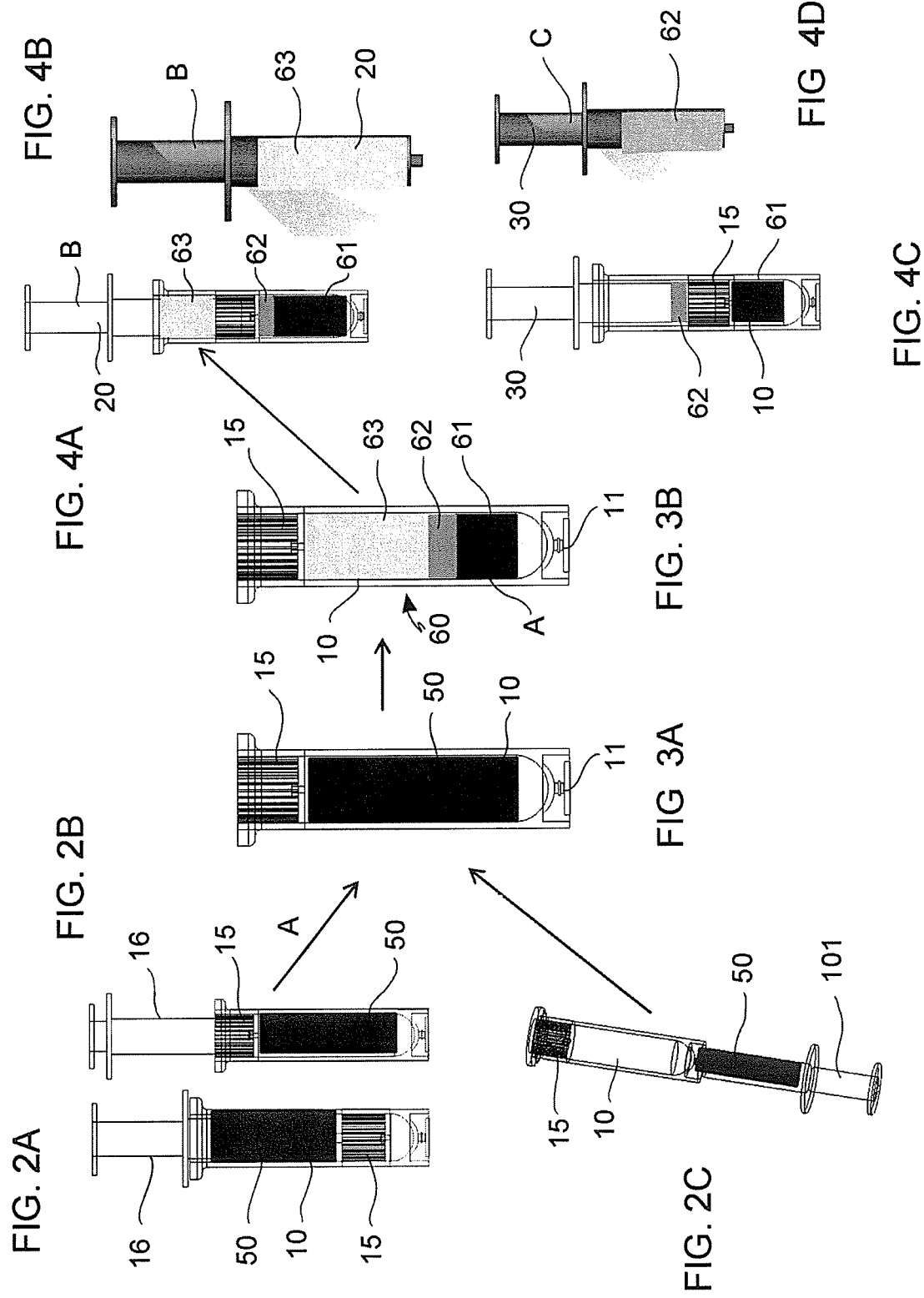

| 5x1500 | PLT Ratio | WBC Ratio | NE Ratio | RBC Ratio | Volume (mL) |
|---|---|---|---|---|---|
| ACP II | 2.5 ± 0.4 | 1.2 ± 0.6 | 0.3 ± 0.2 | 0.1 ± 0.0 | 8.5 ± 2.1 |

FIG. 5(a)

| 12x3000 | PLT Ratio | WBC Ratio | NE Ratio | RBC Ratio | Volume (mL) |
|---|---|---|---|---|---|
| PRP | 4.2 ± 1.3 | 1.5 ± 2.0 | 0.9 ± 1.0 | 0.2 ± 0.1 | 5.0 ± 0.0 |
| PPP | 0.4 ± 0.3 | 0.0 ± 0.0 | 0.0 ± 0.0 | 0.0 ± 0.0 | 16.7 ± 2.9 |

FIG. 6(a)

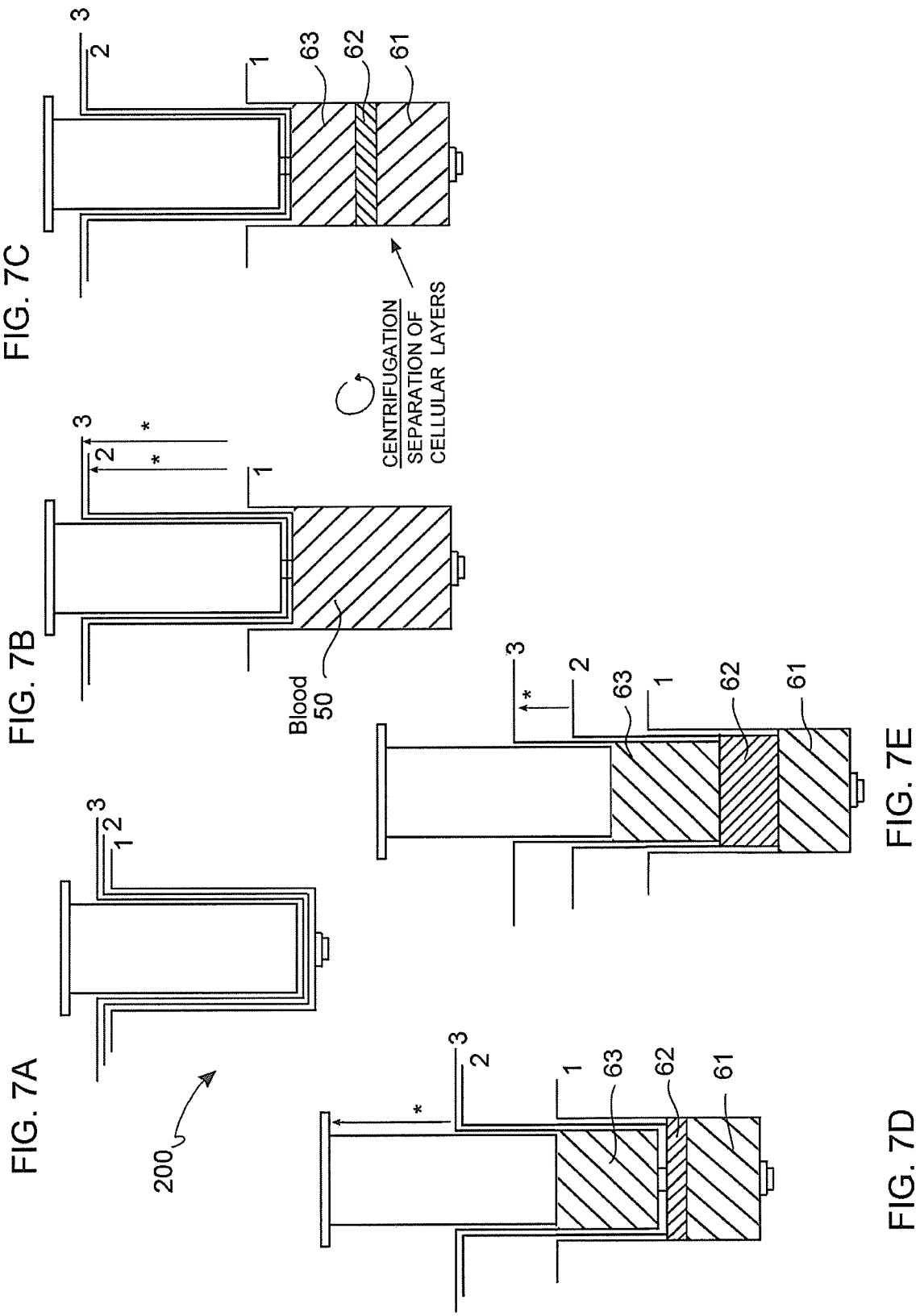

TRIPLE SYRINGE AND METHODS OF MAKING PLATELET-ENRICHED PLASMA AND USE THEREOF

CROSS-REFERENCE TO RELATED APPLICATIONS

This application is a continuation of U.S. application Ser. No. 17/223,277, filed Apr. 6, 2021, which is a continuation of U.S. application Ser. No. 14/605,657, filed Jan. 26, 2015, now abandoned, which claims the benefit of U.S. Provisional Application No. 61/931,956, filed Jan. 27, 2014, the entire disclosures of which are incorporated by reference herein.

FIELD OF THE INVENTION

The present invention relates to methods and apparatus for producing therapeutically active proteins with decreased catabolic cytokines.

BACKGROUND OF THE INVENTION

Systems and methods of producing autologous conditioned plasma (ACP) for treating damaged tissue are known in the art. For example, a system and method of producing ACP in an efficient manner are disclosed in U.S. Pat. No. 8,052,969 issued Nov. 8, 2011, the disclosure of which is incorporated by reference in its entirety herewith. The double-syringe system disclosed in U.S. Pat. No. 8,052,969 consists of two syringes that are in direct fluid communication and that are provided one within the other, for storing and delivering autologous plasma.

There is a need for devices and methods for producing serum and autologous fluid that would produce an increased output, desirably up to 15 mL of ACP or 3 mL of PRP (platelet rich plasma) and 25 mL of PPP (platelet poor plasma). Also needed are devices and methods for producing a high concentration of growth factors, cytokines and proteins in a high volume effluent, and by a simplified method.

SUMMARY OF THE INVENTION

The present invention provides a multi-syringe system that allows for either a larger volume of ACP, or a larger combined output of PRP (platelet rich plasma or plasma enriched with platelets) and PPP (platelet poor plasma). The different outputs are based upon different centrifuge spin regimes and effluent fractions obtained. The multi-syringe system allows for the connection of two or more additional syringes.

The present invention also provides techniques that produce a serum/fluid effluent with various fractions and which have a high concentration of growth factors, cytokines and proteins, in a simplified and fast manner. The fractions may be extracted with the multi-syringe system of the present invention at different sequential times, or at the same time.

A method of the present invention comprises the steps of: (i) providing a multi-syringe including a syringe body (a first or outer syringe body) and a plurality of additional syringe bodies (two or more inner syringe bodies); (ii) providing blood and/or BMA (bone marrow aspirate or bone marrow) into the first syringe body; (iii) subjecting the blood and/or BMA to centrifugation to obtain an effluent comprising various plasma fractions such ACP, PRP or PPP, or combinations thereof; and (iv) removing, from the first syringe body, a specific fraction of the effluent with one of the plurality of additional syringe bodies. The method may further comprise the step of repeating step (iv) for all the specific effluent fractions employing separate syringe bodies.

Other features and advantages of the present invention will become apparent from the following description of the invention, which refers to the accompanying drawings.

BRIEF DESCRIPTION OF THE DRAWINGS

FIGS. 2(a) and 2(b) illustrate how blood/BMA is provided within the first syringe of FIG. 1(a) (from the top) and according to an exemplary embodiment of the present invention.

FIG. 2(c) illustrates how blood/BMA is provided within the first syringe of FIG. 1(a) (from the bottom) and according to another exemplary embodiment of the present invention.

FIGS. 3(a) and 3(b) illustrate subsequent steps of a method of centrifuging the blood/BMA provided within the first syringe of FIG. 1(a), and according to an embodiment of the present invention.

FIGS. 4(a)-4(d) illustrate subsequent steps of a method of extracting two different effluent fractions provided within the first syringe of FIG. 1(a), and with two additional syringes of the multi-syringe system of the present invention, and according to an exemplary embodiment of the present invention (i.e., a triple syringe system).

FIG. 5(a) is a table depicting various ratios of the first effluent of FIG. 5(b).

FIG. 6(a) is a table depicting various ratios of the second effluent of FIG. 6(b).

FIGS. 7(a)-7(e) illustrate subsequent steps of another method of extracting two different effluent fractions provided within another multi-syringe system of the present invention, and according to another exemplary embodiment of the present invention (i.e., a nested triple syringe system).

DETAILED DESCRIPTION OF THE PREFERRED EMBODIMENTS

Figure 1A:
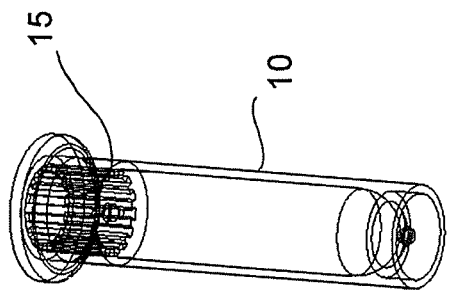
FIG. 1(a) illustrates a perspective view of an exemplary first syringe (outer syringe body provided with a rubber gasket within) of a first exemplary multi-syringe system of the present invention.
Figure 1B:
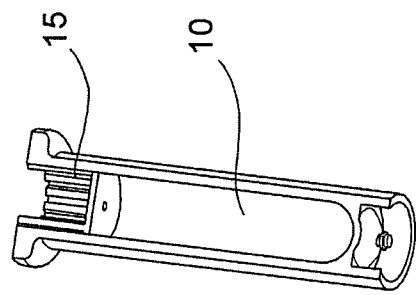
FIG. 1(b) illustrates a schematic perspective view of the first syringe of FIG. 1(a) showing the inner components.
Figure 1C:
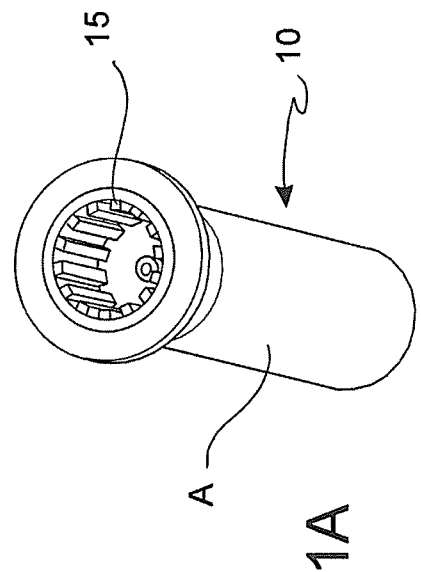
FIG. 1(c) illustrates another perspective view of the first syringe of FIG. 1(a).
Figure 1D:
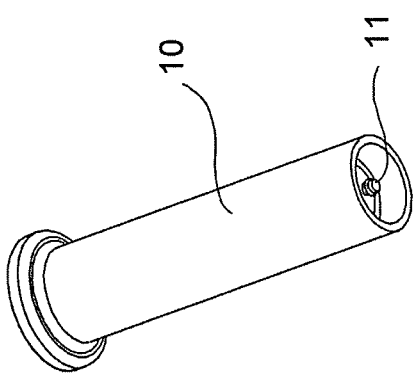
FIG. 1(d) illustrates a cross-sectional view of the first syringe of FIG. 1(a) showing the inner components.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the scope of the present invention.

The present invention provides techniques and devices that produce a serum/fluid effluent with various fractions and which have a high concentration of growth factors, cytokines and proteins, in a simplified and fast manner. The multi-syringe syringe system of the present invention provides compositions (effluents) with increased anabolic and anti-inflammatory cytokines for treatment of human or non-human damaged tissue such as cartilage and neurological tissue.

The multi-syringe system of the present invention allows for either a larger volume of ACP, or a larger combined output of PRP (platelet rich plasma) and PPP (platelet poor plasma). The different outputs are based upon different centrifuge spin regimes and effluent fractions obtained. The multi-syringe system allows for the connection of two or more additional syringes.

The present invention also provides techniques that produce a serum/fluid effluent with various separate fractions and which have a high concentration of growth factors, cytokines and proteins, in a simplified and fast manner. The fractions may be extracted with the multi-syringe system of the present invention at sequential times, or at the same time.

In an exemplary embodiment, the device of the present invention is a triple syringe system that allows for either a larger volume of ACP, or a larger combined output of PRP (platelet rich plasma) and PPP (platelet poor plasma). The different outputs are based upon different centrifuge spin regimes. Currently, the ACP system disclosed in U.S. Pat. No. 8,052,969 (double-syringe system) only produces 5 mL of ACP. The system of the present invention produces up to 15 mL of ACP, or 3 mL of PRP plus 25 mL of PPP. The system of the present invention solves the problem of a larger volume of ACP and with a higher cellular concentration.

An exemplary triple syringe of the present invention comprises inter alia: (i) a first syringe body (an outer tube provided with a luer connector and a rubber gasket to allow connection to additional structures/syringes) having a volume of about 60 cc; and (ii) a plurality of additional syringes that are designed to connect with the first syringe, preferably in sequence to withdraw various effluent plasma fractions from the first syringe, the additional syringes having volumes smaller than about 60 cc. Preferably, each of the additional syringes has a diameter smaller than that of the first syringe, to allow the body of the additional syringes to be at least partially within the body of the outer one.

The additional syringes may be provided as an integral unit with the first syringe body (i.e., may be nested within each other) or may be provided as separate units that can be connected to the first syringe body.

A method of obtaining a plasma enriched with platelets comprises the steps of: (i) providing a multi-syringe including an outer syringe body (a first or distal syringe body) and a plurality of additional syringe bodies (two or more inner syringe bodies or proximal syringe bodies); (ii) providing blood and/or BMA into the first syringe body; (iii) subjecting the blood and/or BMA to centrifugation to obtain an effluent comprising various fractions such autologous plasma, PRP or PPP, or combinations thereof; and (iv) connecting one or more of the plurality of additional syringe bodies to the first syringe body and removing, with the connected additional syringe body, a specific separate fraction of the effluent.

A method of obtaining a plasma enriched with platelets comprises the steps of: (i) providing a multi-syringe including an outer syringe body (a first or distal syringe body) and a plurality of additional syringe bodies (two or more inner syringe bodies or proximal syringe bodies), the plurality of additional syringe bodies being nested within the outer syringe body; (ii) providing blood and/or BMA into the first syringe body; (iii) subjecting the blood and/or BMA to centrifugation to obtain an effluent comprising various fractions such autologous plasma, PRP or PPP, or combinations thereof; (iv) removing, with one of the plurality of additional syringe bodies, a specific separate fraction of the effluent; and (v) removing, with another of the plurality of additional syringe bodies, another specific separate effluent fraction.

The present invention also provides a method of providing autologous growth factors for treatment of connective tissue injuries. An exemplary method comprises inter alia the steps of: (i) providing an extraction assembly comprising a centrifuge, an outer syringe body, and a plurality of inner syringe bodies, each of the plurality of the inner syringes being designed so that at least a portion of the inner syringe body is disposed, in use, within a portion of the outer syringe body; (ii) drawing autologous blood and/or BMA from the animal/patient and introducing the autologous blood and/or BMA into the outer syringe body; (iii) conducting a centrifugation step of the autologous blood/BMA in the outer syringe body to obtain an effluent with various plasma fractions such as ACP, PPP and PRP fractions; (iv) removing, with a first of the plurality of inner syringe body, a first effluent fraction (for example, PPP) from the outer syringe body; (v) removing, with a second of the plurality of inner syringe body a second effluent fraction (for example, PRP) from the outer syringe body, the second effluent fraction being different from the first effluent fraction; and (vi) delivering at least a portion of the first and/or second effluents into a damaged tissue of the animal, by employing the first and/or second of the plurality of inner syringe bodies.

The present invention also provides a method of obtaining at least 3 mL of PRP and at least 25 mL of PPP by the steps of: (i) providing an apparatus comprising a centrifuge and a triple syringe, the triple syringe including an outer syringe body with a volume of about 60 cc, and two additional inner syringe bodies (a second syringe body and a third syringe body) with volumes smaller than about 60 cc that are designed to connect, in use, with the outer syringe body; (ii) providing autologous blood or BMA into the outer syringe body; (iii) subjecting the autologous blood to centrifugation by hard spin (about 12×3000) to obtain a PPP fraction and a PRP fraction; (iv) removing, with the second syringe body, the PPP fraction from the first syringe body; (v) removing, with the third syringe body, the PRP fraction from the first syringe body; and (vi) delivering at least a portion of the PPP fraction and/or of the PRP fraction into a damaged tissue of the animal, by employing the second and/or third syringe body.

Referring now to the drawings, where like elements are designated by like reference numerals, FIGS. 1(a)-7(e) illustrate components and structural parts of exemplary multi-syringe system 100, 200 of the present invention for providing platelet-enriched plasma (ACP, or PPP and PRP), for treatment of human or non-human damaged tissue such as cartilage and neurological tissue. Although, for simplicity, reference to the multi-syringe system 100, 200 will be made as to a triple syringe, triple syringe system or tri-syringe 100, 200, the invention is not limited to this exemplary-only embodiment and encompasses any number of additional syringes to be employed with the outer (first) syringe body, depending on the number of effluent fractions to be removed, and as detailed below.

Exemplary triple syringe system 100 of the present invention consists of three syringes 10, 20, 30 (also labeled A, B, C) that are used in sequential order to extract various effluent fractions, for example, ACP, or PRP and PPP, and as detailed below. First syringe 10 of the system/apparatus 100 is provided in direct fluid communication with the second syringe 20 or the third syringe 30, the second and third syringes 20, 30 being provided, in use, within at least a portion of the body of the first syringe 10. The second and third syringes 20, 30 have a diameter smaller than that of the first syringe 10, to allow the body of the second or third syringe to be at least partially located within the larger first syringe body 10.

As detailed below, outer syringe body 10 (distal syringe) is used to store the ACP, or PPP and PRP, formed as the result of the centrifugation of blood, while inner syringe body 20 and inner syringe body 30 (proximal syringes) are used to remove/extract at least part of ACP, or PPP or PRP, from the outer syringe body 10 and to further inject the removed part of ACP, or PPP or PRP into the damaged tissue.

Triple syringe system 100 allows for either (i) a larger volume of ACP, or (ii) a combined output of PRP (platelet rich plasma) plus PPP (platelet poor plasma). The different outputs are based upon different centrifuge spin regimes. Currently, the Arthrex ACP system (the double syringe system) only produces 5 mL of ACP and is devoid of any PPP. The new system 100 of the present invention produces up to 15 mL of ACP, or 3 mL of PRP plus 25 mL of PPP.

FIGS. 1(*a*)-1(*d*) illustrate a first or outer syringe body 10 (distal syringe or syringe A) in the form of an outer plastic tube 10 formed of polypropylene, polycarbonate, or similar materials. Outer syringe body 10 (distal syringe) may be in the form of a conventional syringe for obtaining a blood sample, including a body having an enlarged volume, preferably of at least 60 cc, and also configured to accommodate a flow-through plunger 16 (FIGS. 2(*a*) and 2(*b*)). A shaft or plunger rod 16 provided within the body 10 permits the syringe body 10 to be filled with the fluid sample 50 (for example, blood, bone marrow, and/or BMA, etc.) and store it therein.

Outer syringe body 10 is also provided with a tip or coupling device 11 provided at the most distal end of body 10. Coupling device 11 may be a luer-lock type cap or a twist-on locking device, and is configured to receive a syringe needle or the luer-lock coupling of a three-way stop cock. Outer syringe body 10 (distal syringe) is also provided with a small rubber gasket 15 that allows for connection of an additional "inner syringe" 20, 30 (syringe B, C), as shown in FIGS. 4(*a*)-4(*d*).

Connection of syringe 20, 30 to the rubber gasket 15 creates a seal so that autologous fluid 50 (whole blood, bone marrow, etc.) can be pulled into the outer tube 10 (tube A).

FIGS. 2(*a*)-2(*c*) illustrate exemplary embodiments of how fluid 50 is provided into the syringe body 10 for further centrifugation. Fluid 50 (e.g., blood or BMA 50) may be injected into tube 10 (A) in two ways, either from the top or from the bottom. FIGS. 2(*a*) and 2(*b*) illustrate introduction of the fluid 50 from the top of the syringe body 10, i.e., through rubber gasket 15 and into the syringe. Pulling on plunger 16 permits body 10 to be filled with the fluid 50. FIG. 2(*c*) illustrates introduction of the fluid 50 from the bottom of the syringe body 10, i.e., through coupling device/ luer 11 and with an additional syringe 101 or similar device. Alternatively, first syringe 10 may be itself employed to directly draw blood or bone marrow from patient.

Subsequent to the fluid (blood/BMA) injection into the tube 10 (through rubber gasket 15 or coupling device 11), the syringe body 10 containing fluid 50 (without plunger 16) is centrifuged. A luer cap (not shown) is provided on top of the syringe body 10 adjacent the rubber gasket 15 to allow centrifugation (FIG. 3(*a*)).

FIG. 3(*b*) illustrates syringe body 10 with fluid 50 after the centrifugation, i.e., with obtained effluent 60. Depending on the degree of centrifugation, i.e., on whether soft spin (to obtain ACP) or hard spin (to obtain PPP and PRP) is applied, different cellular fractions can be isolated. The embodiment shown in FIG. 3(*b*) illustrates effluent 60 with three different fractions 61, 62, 63 obtained as a result of hard spin, for example, 12×3000, to obtain exemplary PPP fraction 63 and exemplary PRP fraction 62.

FIGS. 4(*a*)-4(*d*) illustrate subsequent steps of a method of extracting two different effluent fractions, i.e., fractions 62, 63 provided within the first syringe 10, and with two additional syringes 20, 30 of the multi-syringe system 100 of the present invention.

Second syringe 20 (inner syringe 20 or syringe B) is connected to first syringe 10 as shown in FIGS. 4(*a*) and 4(*b*) to pull off PPP 63 (PPP fraction 63). Second syringe 20 is then removed and the PPP 63 (PPP fraction 63) may be employed for various tissue treatments.

Third syringe 30 (inner syringe 30 or syringe C) is then connected to the first syringe 10 to draw off the remaining PRP 62 (PRP fraction 62), as shown in FIGS. 4(*c*)-4(*d*). In an exemplary-only embodiment, the first syringe 10 (A) has a volume of about 60 cc, the second syringe 20 (B) has a volume of about 30 cc and the third syringe 30 (C) has a volume of about 10 cc. This design permits the system 100 of the present invention to obtain a high volume effluent 60 that contains 3 mL of PRP (fraction 62) and 25 mL of PPP (fraction 63). The plunger of syringe 10 is designed to allow different sizes of syringes (i.e., 60, 30, 10 and/or 5 cc syringes) to be attached thereto.

As the syringe system 100 allows for the connection of two or more inner syringes, different cellular fractions can be isolated, depending on the requirements and specifics of the surgery. The triple syringe produces a larger volume of PPP and a concentrated PRP.

FIG. 5(*b*) illustrates results of the process of using the first syringe 10 of the system 100 of present invention, using soft spin, to obtain effluent 70 with ACP 72 on top. An additional syringe (for example, second syringe 20) is connected to withdraw ACP fraction 72 having an increased harvest volume of about 15 mL. FIG. 5(*a*) is a table depicting various ratios of the ACP fraction 72 of effluent 70 of FIG. 5.

Figure 6B:
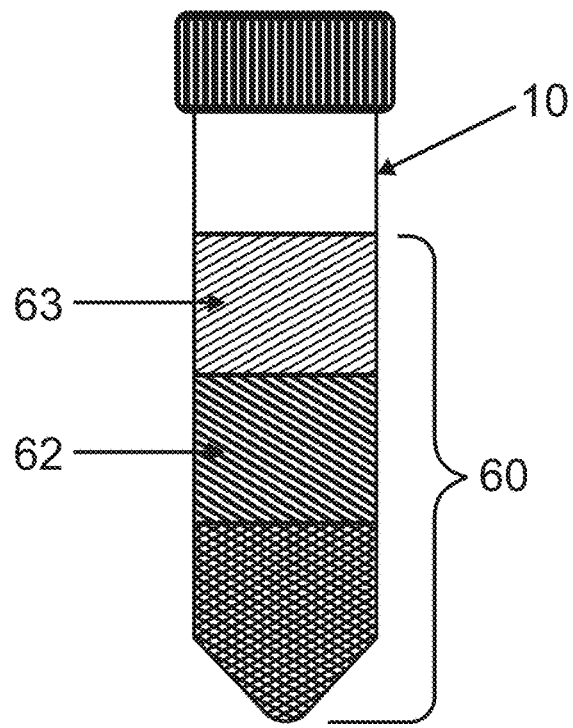
FIG. 6(b) illustrates the first syringe of FIG. 1(a) after hard spin centrifugation and with a second effluent containing various fractions.

FIG. 6(*b*) illustrates the first syringe 10 after hard spin centrifugation and with second effluent 60 containing various fractions, i.e., PPP fraction 63 and exemplary PRP fraction 62. FIG. 6(*a*) is a table depicting various ratios of the PPP fraction 63 and exemplary PRP fraction 62 of the effluent 60 of FIG. 6(*b*).

FIGS. 7(*a*)-7(*e*) illustrate exemplary triple syringe 200 consisting of three nested syringes (nested syringe bodies) 1, 2, 3. The second syringe 2 is nested within the first syringe 1, and the third syringe 3 is nested within the second syringe 2. The second syringe 2 and the third syringe 3 are also in fluid communication with the first syringe 1.

Blood or bone marrow aspirate 50 is inserted within syringe 1 (FIG. 7(*b*)) and subjected to centrifugation for separating of cellular layers, and to obtain effluent fractions 61, 62, 63. The smaller diameter syringe 3 is then employed to extract effluent fraction 63 ((FIG. 7(*d*)) and syringe 2 to extract effluent fraction 62. The symbol "\*" indicated that syringes 1 and 2 can be removed for/with different cellular content.

After centrifugation, syringe 1 could have the red blood cell cellular component. Syringe 3 could have the platelet poor component and syringe 2 could have the concentrated platelet component and white blood cell component. As detailed above with reference to system 100, depending on how fast the device is centrifuged and how aggressive each plunger is pulled, different concentrations of cells can be found in each syringe. Syringes 2 and 3 can be removed from syringe 1.

Exemplary syringes 10, 20, 30, 1, 2, 3 of the system 100, 200 of the present invention may be provides as part of a kit (tray) incorporating additional syringes having different dimensions and volumes, to accommodate extraction of the various fractions of the effluents obtained as a result of at least one rotational step as part of centrifugation. The kit may include a centrifuge to allow medical personnel (surgeon) to obtain the effluent fractions in situ (at the surgical site) and then conduct at least one procedure of therapeutic usage of the fraction (ACP, PPP or PRP) at an arthroscopic site, for example.

The ACP, PPP and PRP fractions of the present invention may be prepared/obtained directly in a doctor's office as well as in the operating room. A main advantage of the method of obtaining the ACP, PPP and PRP fractions of the present invention is that the multi-syringe 100, 200 enables to transfer plasma, PPP or PRP from the bigger syringe into smaller syringes and then using the smaller syringes on various patients and/or various surgical sites. Further, as no activator (such as thrombin, for example) is added to the extracted blood to initiate or catalyze a platelet release reaction (i.e., no activator or substance to release material from the platelets is added prior to, or during, the centrifugation process), the risk of contamination is additionally reduced and the complexity of the procedure is decreased.

According to an exemplary embodiment, and if desired, activators (such as thrombin, for example) may be added subsequent to the harvesting of the effluent fractions (i.e., subsequent to the centrifugation process) to force the platelets to secrete their growth factors.

A method of obtaining platelet enriched plasma with the system 100 of the present invention comprises the steps of: (i) providing a multi-syringe assembly comprising a first syringe having a first body with a first diameter; a second syringe having a second body with a second diameter smaller than the first diameter; and a third syringe having a third body with a third diameter smaller than the first diameter; (ii) introducing blood or bone marrow aspirate into the first syringe; (iii) subjecting the first syringe to centrifugation to obtain platelet enriched plasma containing a plurality of plasma fractions; (iv) connecting the second syringe to the first syringe so that the first syringe is in direct fluid communication with the second syringe, and the second syringe is located partially within the first syringe, and transferring a first fraction of the plurality of plasma fractions from the first syringe to the second syringe; and (v) connecting the third syringe to the first syringe, so that the first syringe is in direct fluid communication with the third syringe, and the third syringe is located partially within the first syringe, and transferring a second fraction of the plurality of plasma fractions from the first syringe to the third syringe.

A method of surgical treatment of connective tissue injury with system 100, 200 of the present invention comprises the steps of: (i) providing a multi-syringe system comprising a first syringe having a first body with a first diameter and a volume of about 60 cc; a second syringe having a second body with a second diameter smaller than the first diameter; and a third syringe having a third body with a third diameter smaller than the first diameter; (ii) introducing about 60 mL of autologous blood or bone marrow aspirate into the first syringe so that the autologous blood or bone marrow aspirate is temporarily stored within the first syringe; (iii) introducing the first syringe into a centrifuge and centrifuging the first syringe to obtain a PPP fraction and a PRP fraction in the first syringe; (iv) transferring the PPP fraction from the first syringe to the second syringe; (v) disconnecting the second syringe with the PPP fraction from the first syringe; (vi) subsequently, transferring the PRP fraction from the first syringe to the third syringe; (vii) disconnecting the third syringe with the PRP fraction from the first syringe; and (viii) delivering at least one of the PPP fraction and the PRP fraction to the connective tissue, wherein the PPP fraction has a harvest volume of about 25 mL and the PRP fraction has a harvest volume of about 3 mL.

Benefits of the system 100, 200 of the present invention include as follows:
  Can perform soft or hard centrifugation on device, i.e., more volume of ACP (soft spin) or PRP/PPP (hard spin);
  Performs better when compared to previously-tested devices;
  Could apply design into IRAP systems.

Additional growth factors (including autologous growth factors produced from a patient's own blood, obtained by a centrifugation process) and/or additional antiseptic chemicals and/or antibiotics and/or electrolytes may be added to the effluent fractions. The additional antiseptics and/or the antibiotics and/or the electrolytes will typically be present in the plasma (ACP, PPP or PRP) in a predetermined concentration range, which will be dependent upon the particular tissue site and application, as well as the specific activity of the antiseptic and/or the antibiotic and/or the electrolytes. The antibiotics may be selected from the group consisting of a neosporin, vancomycin and gentamycin, and combinations thereof.

The fractions may further comprise one or more additional components which promote or enhance the wound healing effectiveness of the autologous growth factors. As such, hormones or site-specific hybrid proteins may be incorporated in the autologous blood suspension to maximize the availability of the autologous growth factors at the tissue to be repaired and/or to potentiate wound healing.

According to another embodiment of the present invention, the plasma fractions may additionally comprise anti-coagulants such as, for example, citrate, acid-citrate dextrose (ACD), citrate-phosphate-dextrose (CPD), or ethylene diamine tetra-acetic acid (EDTA). Heparin may be also added in an amount sufficient for the prevention of thrombin activity during the processing steps. Proteolytic enzyme inhibitors, such as aprotinin E-aminocaproic acid or tranexamic acid may be added to prevent proteolytic degradation of the autogenous growth factors.

According to yet another embodiment of the present invention, the plasma fractions may further comprise one or more vitamins such as vitamin E, vitamin A and other retinoids. Vitamins are known to have wound healing and antioxidant properties. Alternatively, or additionally, non-vitamin anti-oxidants may be included in the blood suspension. Non-limiting representative examples of such anti-oxidants include 13-carotene.

Preferably, the plasma fractions in the inner syringe body 20, 30, 2, 3 contain an amount of thrombocytes that provides enhancement of the healing of the damaged tissue and promote tissue growth. Once plasma fraction is injected into the tissue with the syringe 20, 30, 2, 3 the thrombocytes excrete growth factors that will trigger/enhance the healing process. The high level of thrombocytes also enhances the healing of the damaged tissue and tissue growth.

Figure 5B:
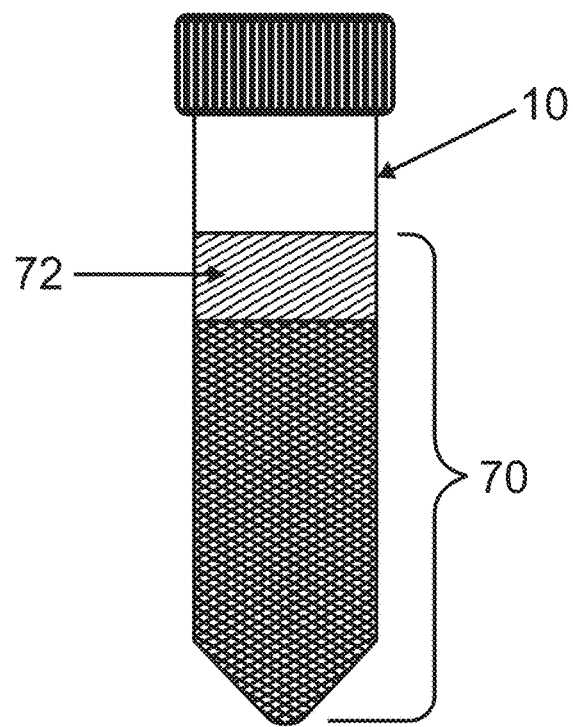
FIG. 5(b) illustrates the first syringe of FIG. 1(a) after soft spin centrifugation and with a first effluent.

Autologous conditioned plasma (ACP) 72 (shown in FIG. 5(b)) may be obtained by subjecting a volume of about 60 ml blood (of a donor) to a soft spin (about 5×1500) to obtain a harvest volume of about 15 mL autologous conditioned plasma (ACP), which is a very large output obtained by a single process.

The ACP, PPP or PRP fractions may be employed for treatment of human joints, for example, a shoulder joint, a hip joint, an elbow joint, or a knee joint. The plasma fractions may be employed for treatment of various cartilage or tendon damage or diseases (as long as the cartilage is partially remaining) such as, for example:

Chondromalacia I'-111° (according to Outerbridge);
  a. Large and small joints of upper and lower extremities; and
  b. Small vertebral joints.
Traumatologic cartilage damage;
Post-op situations e.g. flake fracture refixation, microfractures and/or cartilage transplantation (ACT or OATS); and
Tendinosis and ligamentosis.

The plasma fractions may be also employed in neurosurgery applications, such as, for example:

Radiculitis and radiculopathy of the cervical and lumbar spine;
Syndrome of the vertebral column facets; and
Other spinal applications, e.g., degeneration of spinal disk and erosive osteochondrosis.

The plasma fractions extracted with the inner syringe body 20, 30, 2, 3 may be administered to a patient by injection once a week, for a total of about six weeks. In individual cases, however, the plasma fractions may be administered twice a week. In neurological applications, the plasma fractions of the present invention may be provided by assisted injections upon the relevant nerve roots. Alternatively, the plasma fractions may be provided on or between the vertebral joints.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents within the scope of the invention.

Accordingly, the invention is not to be considered as limited by the foregoing description.

What is claimed is:

1. A method of obtaining autologous conditioned plasma (ACP), comprising:
   (a) introducing autologous blood or bone marrow aspirate into a first body of a first syringe of a nested set of syringes, wherein the nested set of syringes comprises the first syringe having the first body with a first diameter; a second syringe having a second body with a second diameter smaller than the first diameter; and a third syringe having a third body with a third diameter smaller than the second diameter; wherein the first syringe is in direct fluid communication with the second syringe and the third syringe, wherein the second syringe body is located partially within the body of the first syringe, and wherein the third syringe body is located partially within the body of the second syringe;
   (b) subjecting the nested set of syringes to centrifugation to obtain two or more of blood or bone marrow fractions including a first fraction and a second fraction; and
   (c) transferring part of the first fraction from the first syringe to the third syringe; and transferring part of the first fraction from the first syringe to the second syringe, wherein the first fraction is ACP, such that the ACP is obtained in the second syringe and the third syringe.

2. The method of claim 1, further comprising removing the second syringe and third syringe from the first syringe, wherein the ACP contained within the second syringe, and/or the ACP contained within the third syringe is used for treating at least a portion of a damaged tissue to facilitate healing of the damaged tissue.

3. The method of claim 2, wherein the damaged tissue is a joint.

4. The method of claim 2, wherein the damaged tissue is a nerve root or a vertebral joint.

5. The method of claim 2, wherein the damaged tissue is a damaged tendon.

6. The method of claim 1, wherein the first body has a volume of about 60 mL.

7. The method of claim 1, wherein the first syringe comprises a gasket.

8. The method of claim 1, comprising introducing the bone marrow aspirate into the body of the first syringe.

9. The method of claim 1, further comprising adding thrombin to the ACP of the second syringe and/or the ACP of the third syringe.

10. The method of claim 1, further comprising adding an anticoagulant to the ACP of the second syringe and/or the ACP of the third syringe.

11. A method of surgical treatment of connective tissue injury, comprising:
   (a) introducing autologous blood or bone marrow aspirate into a first syringe of a nested set of syringes, wherein the nested set of syringes comprises the first syringe having a first body with a first diameter; a second syringe having a second body with a second diameter smaller than the first diameter; and a third syringe having a third body with a third diameter smaller than the second diameter; wherein the first syringe is in direct fluid communication with the second syringe and the third syringe, wherein the second syringe body is located partially within the body of the first syringe, and wherein the third syringe body is located partially within the body of the second syringe, so that the autologous blood or bone marrow aspirate is temporarily stored within the first syringe;
   (b) centrifuging the nested set of syringes to obtain an ACP fraction and a red blood cell fraction in the first syringe; and
   (c) transferring part of the ACP fraction from the first syringe to the second syringe, transferring part of the ACP fraction from the first syringe to the third syringe, disconnecting the third syringe and second syringe from the first syringe, and delivering the ACP fraction of the second syringe and/or the ACP fraction of the third syringe to a connective tissue.

12. The method of claim 11, wherein the ACP fraction in the second syringe and the ACP fraction of the third syringe have a total harvest volume of about 15 mL.

13. The method of claim 11, wherein the first syringe comprises a gasket.

14. The method of claim 11, comprising introducing the bone marrow aspirate into the body of the first syringe.

15. The method of claim 11, further comprising adding thrombin to the ACP fraction of the second syringe and/or the ACP fraction of the third syringe.

16. The method of claim 11, further comprising adding an anticoagulant to the ACP fraction of the second syringe and/or the ACP fraction of the third syringe.

* * * * *